United States Patent
Yoo et al.

(10) Patent No.: US 7,371,775 B2
(45) Date of Patent: May 13, 2008

(54) 7-CARBOXYMETHYLOXY-3',4',5-TRIMETHOXY FLAVONE MONOHYDRATE, THE PREPARATION METHOD AND USES THEREOF

(75) Inventors: Moohi Yoo, Seoul (KR); Dong Sung Kim, Seoul (KR); Yong Duck Kim, Kyunggi-do (KR); Wonbae Kim, Seoul (KR)

(73) Assignee: Dong-A Pharmaceuticals Co., Ltd (KR)

( * ) Notice: Subject to any disclaimer, the term of this patent is extended or adjusted under 35 U.S.C. 154(b) by 270 days.

(21) Appl. No.: 10/564,128

(22) PCT Filed: Sep. 4, 2004

(86) PCT No.: PCT/KR2004/002247

§ 371 (c)(1),
(2), (4) Date: Jan. 10, 2006

(87) PCT Pub. No.: WO2005/023244

PCT Pub. Date: Mar. 17, 2005

(65) Prior Publication Data

US 2006/0178428 A1    Aug. 10, 2006

(30) Foreign Application Priority Data

Sep. 4, 2003   (KR) .................... 10-2003-0061938

(51) Int. Cl.
*A61K 31/353*   (2006.01)
*C07D 311/30*   (2006.01)

(52) U.S. Cl. ...................... 514/456; 549/403
(58) Field of Classification Search ............... 549/403; 514/456
See application file for complete search history.

(56) References Cited

FOREIGN PATENT DOCUMENTS

| | | |
|---|---|---|
| KR | 96-30494 | 4/1998 |
| KR | 99-41205 | 4/2001 |
| WO | WO 98/04541 | 2/1998 |

OTHER PUBLICATIONS

Mizui, Takuji, et al., Effect of Polyamines on Acidified . . . , Japan, J. Pharmacol. 33, pp. 939-945, (1983).
Shibata, Yoshimi, et al., Endoscopic Scoring System for Experimental . . . , Dig. Endosc. vol. 5, pp. 13-17, 1993.
Wallace, John L., Release of Platelet-Activating Factor (PAF) and Accelerated . . . , Can. J. Physiol. Pharmacol. vol. 66, pp. 422-425.
Moyana, Terence N., et al., Carrageenan-Induced Intestinal . . . , Ann. of Clinical and Laboratory Science, vol. 20, No. 6.

*Primary Examiner*—Bernard Dentz
(74) *Attorney, Agent, or Firm*—Lucas & Mercanti, LLP (57) ABSTRACT

The present invention relates to 7-carboxymethyloxy-3',4', 5-trimethoxy flavone.monohydrate which is a non hygroscopic product suitable for the preparation of metered dose of 7-carboxymethyloxy-3',4',5-trimethoxy flavone having protective activity for gastrointestinal tract including the colon, and a preparation method and uses thereof. 7-carboxymethyloxy-3',4',5-trimethoxy flavone.monohydrate of the present invention has advantages such as mucus protecting activity for gastrointestinal tract including the colon, convenience for handling and storage under ordinary humidity owing to its non-hygroscopicity, and ability to contain an active compound consistently for the formulation production of a medicine. In addition, the preparation method of 7-carboxymethyloxy-3',4',5-trimethoxy flavone.monohydrate of the present invention reduces long steps of total synthesis and requires mild conditions for the production of a compound because autoclave condition is not necessary for methylation in this case, and makes mass-production possible without any purification process such as recrystallization or column chromatography.

17 Claims, 5 Drawing Sheets

7-CARBOXYMETHYLOXY-3',4',5-TRIMETHOXY FLAVONE MONOHYDRATE, THE PREPARATION METHOD AND USES THEREOF

This patent application claims the benefit of priority from Korean Patent Application No. 10-2003-0061938 filed Sep. 4, 2003 through PCT Application Ser. No. PCT/KR2004/002247 filed Sep. 4, 2004 the contents of which are incorporated herein by reference.

TECHNICAL FIELD

The present invention relates to 7-carboxymethyloxy-3', 4',5-trimethoxy flavone.monohydrate, and a preparation method and uses thereof, more precisely, to 7-carboxymethyloxy-3',4',5-trimethoxy flavone.monohydrate which is a non hygroscopic product suitable for the preparation of metered dome of 7-carboxymethyloxy-3',4',5-trimethoxy flavone having mucus protecting activity in the gastrointestinal tract including colon, and to a preparation method and uses thereof.

BACKGROUND ART 7-carboxymethyloxy-3',4',5-trimethoxy flavone represented by formula 2 has been known to have mucus protecting activity in gastrointestinal tract including colon (WO 98/04541, Korea Patent No. 96-30494). This flavone showed therapeutic effects on gastrointestinal diseases such as gastritis or gastric ulcer, and inflammatory intestinal diseases such as ulcerative colitis or Crohn's disease.

[Formula 2]

The present inventors discovered that 7-carboxymethyloxy-3',4',5-trimethoxy flavone represented by the above formula 2 is hygroscopic. Each dose of a medicine should include a specified amount of an active compound. However, in case the active compound is hygroscopic, meaning tendency to absorb moisture from atmosphere, it is not easy to make the metered dose correspond to the specified amount of the active compound consistently. And also a hygroscopic material give rise to the difficulty in handling and storage condition. That is, the characteristic as a hygroscopic material is a big disadvantage for the production as a medicine. Thus, the present inventors have tried hard to find a stable form of the active ingredient without hygroscopicity.

A synthetic method for 7-carboxymethyloxy-3',4',5-trimethoxy flavone was described in WO 98/04541 (Korea Patent No. 96-30494), as shown in scheme 1 consisting of 9 step-total synthesis started from 2,4,6-trihydroxy acetophenone.

[Scheme 1]

2

3

3a

This synthetic method is useful for the production of the derivatives of various different substituents. But 2,4,6-trihydroxy acetophenone used as a starting material is so expensive that it is not economical for the industrial production, furthermore considering long 9 step reaction and low yield make the matters worse. In order to eliminate benzyl group used for a protecting group of hydroxyl, the hydrogen gas under pressure in the presence of palladium catalyst (Pd/C) was used twice in Scheme 1. For this hydrogenation reaction a special device to handle the pressured gas is necessary and palladium catalyst is also very expensive, making the processes complicate and uneconomical. The industrial use of hydrogen gas and catalyst is also dangerous.

Another preparation method for 7-carboxymethyloxy-3',4',5-trimethoxy flavone was described in Korea patent No. 99-41205, as shown in scheme 2.

[Scheme 2]

In the above processes, a compound of formula 3 was reacted with methylating reagent under the basic condition. Conversion of hydroxyl groups in carbon-3' and carbon-5 of the formula 3 into methoxy groups followed by acid treatment furnished a compound of formula 3a. The mixture of 3',5,7-trihydroxy-4'-methoxy flavone-7-rutinoside of formula 3 in dimethylformamide, potassium carbonate and iodomethane were stirred in closed vessel at 60° C. for 48 hours, leading to the conversion of hydroxyl groups of carbon-3' and carbon-5 of formula 3 into methoxy groups. After treating the resultant compound with acid gave the compound of formula 3a.

Then, hydroxyl group of carbon-7 of the compound of formula 3a was converted into alkyloxycarbonylmethyloxy group to give a compound of formula 3b. The deprotection of carboxyl group furnished a compound of formula 2.

The methylation mentioned above needs a special device and is dangerous because the reaction must be carried out in a closed vessel causing huge pressure. So the mass-production of a compound becomes inefficient. In order to give the compound of formula 3b from the compound of formula 3a, purification with column chromatography was inevitable. Therefore, the above preparation method invites danger and high cost.

Thus, the present inventors discovered that 7-carboxymethyloxy-3',4',5-trimethoxy flavone.monohydrate is a non-hygroscopic compound which is more suitable for the preparation of metered dose than 7-carboxymethyloxy-3',4',5-trimethoxy flavone.anhydride, and established a synthetic method thereof which is more economical, convenient and adequate for mass-production as well as devoid of costly purification procedure of column chromatography.

DISCLOSURE

Technical Solution

It is an object of the present invention to provide 7-carboxymethyloxy-3',4',5-trimethoxy flavone.monohydrate, a non-hygroscopic compound which is characterized as chemically stable under ordinary or severe indoor humidity, a preparation method and uses thereof.

BEST MODE

The present invention provides 7-carboxymethyloxy-3',4',5-trimethoxy flavone.monohydrate represented by the following formula 1.

[Formula 1]

The present invention also provides 7-carboxymethyloxy-3',4',5-trimethoxy flavone.solvate represented by the following formula 1a.

[Formula 1a]

7-carboxymethyloxy-3',4',5-trimethoxy flavone.monohydrate, represented by above formula 1 according to the present invention is a monohydrate of 7-carboxymethyloxy-3',4',5-trimethoxy flavone.anhydride represented by above formula 2 and has similar pharmaceutical effects to that. Particularly, it was described in WO 98/04541 (Korea Patent No. 96-30494) that 7-carboxymethyloxy-3',4',5-trimethoxy flavone.anhydride has mucus protecting activity for gastrointestinal tract including the colon. And the compound of formula 1 of the present invention has also proved to have mucus protecting activity for gastrointestinal tract including colon. For example, a compound of the present invention showed anti-colitic effect when administered orally or rectally to a inflammatory bowel disease model induced by trinitrobenzene sulfonic acid. And also the compound of the present invention showed protective effect on the damaged gastric mucous membrane.

The compound of the above formula 1 according to the present invention showed no hygroscopicity contrast to 7-carboxymethyloxy-3',4',5-trimethoxy flavone.anhydride did. As explained in experimental example 1, when 7-carboxymethyloxy-3',4',5-trimethoxy flavone.monohydrate and its corresponding anhydride were placed under the same conditions (25° C., 75% relative humidity), the weight of the anhydride was increased by 4.6%, indicating that the anhydride absorbed moisture to convert into the monohydrate. It was also observed that a solvate, in particular ethanol solvate, was converted into monohydrate under the same conditions of 25° C., 75% relative humidity. However, the monohydrate of the present invention showed no weight change, indicating that the monohydrate of the present invention is very stable substance having no hygroscopicity.

Therefore, the monohydrate compound of the present invention enables the metered dose to keep a specified amount of an active compound consistently, which is a great advantage for the formulated production of a medicine containing 7-carboxymethyloxy-3',4',5-trimethoxy flavone as an effective ingredient. It is another advantage of the compound of the present invention to facilitate handling and storage of a medicine containing the same.

The present invention also provides a synthetic method of 7-carboxymethyloxy-3',4',5-trimethoxy flavone of the below formula 2 using 3',5,7-trihydroxy-4'-methoxy flavone-7-rutinoside of the below formula 3 as a starting material as shown in scheme 3.

[Scheme 3]

3

4

5

(Wherein, R' is a carboxyl protecting group selected from a group consisting of ethyl, methyl, t-butyl, benzyl, trichloroethyl and silyl.)

The present invention also provides a preparation method of 7-carboxymethyloxy-3',4',5-trimethoxy flavone.monohydrate of the formula 1, which is characterized by the process of stirring the compound of formula 2 obtained from the step 4 of the scheme 3 in a medium containing water as shown in the scheme 4.

The present invention also provides a preparation method of 7-carboxymethyloxy-3',4',5-trimethoxy flavone.monohydrate of the formula 1, in which the compound of formula 2 obtained from the step 4 of the above scheme 3 was just placed under humidified atmosphere as shown in the scheme 5.

The present invention also provides a preparation method of 7-carboxymethyloxy-3',4',5-trimethoxy flavone.monohydrate of the formula 1, which includes the step of stirring the compound of formula 2 obtained from the step 4 of the above scheme 3 in anhydrous alcohol to give 7-carboxymethyloxy-3',4',5-trimethoxy flavone.solvate of the formula 1a and leaving this solvate of formula 1a under humidified atmosphere as shown in the scheme 6.

[Scheme 6]

More precisely, a preparation method of 7-carboxymethyloxy-3',4',5-trimethoxy flavone.monohydrate according to the present invention, represented by formula 1, consists of following steps: 1) hydroxyl group of carbon-3' of 3',5,7-trihydroxy-4'-methoxy flavone-7-rutinoside of formula 3 is converted into methoxy group, and followed by acid treatment; 2) the resultant compound is reacted with alpha-haloacetate in which carboxyl group is protected; 3) hydroxyl group of carbon-5 of 7-alkyloxycarbonylmethyloxy-5-hydroxy-3',4'-dimethoxy flavone of formula 5 is converted into methoxy group; 4) protecting group of carboxyl group is deprotected to give 7-carboxymethyloxy-3',4',5-trimethoxy flavone; and 5) the resultant compound is contacted with a medium containing water or just left under humidified atmosphere.

Another preparation method of 7-carboxymethyloxy-3',4',5-trimethoxy flavone.monohydrate of the present invention, represented by formula 1, consists of the steps of reacting 7-carboxymethyloxy-3',4',5-trimethoxy flavone with anhydrous alcohol to give 7-carboxymethyloxy-3',4',5-trimethoxy flavone.solvate, and placing the product under humidified atmosphere.

Particularly, the preparation method of 7-carboxymethyloxy-3',4',5-trimethoxy flavone.monohydrate of the present invention, represented by formula 1, consists of following steps:

(1) The compound of formula 3 is reacted with methylating reagent in the presence of base to convert hydroxyl group of carbon-3' into methoxy group, and followed by acid treatment to prepare a compound of formula 4 (Step 1);

(2) The compound of formula 4 is reacted in the presence of base with alpha-haloacetate in which the carboxyl group is protected to give a compound of formula 5 (Step 2);

(3) The compound of formula 5 is reacted with methylating reagent to convert hydroxyl group of carbon-5 into methoxy group, resulting in a compound of formula 6 (Step 3);

(4) Deprotection of the compound of formula 6 is carried out, resulting in 7-carboxymethyloxy-3',4',5-thrimethoxy flavone of formula 2 (Step 4); and (5) The compound of formula 2 is stirred in a medium containing water or placed under humidity to prepare 7-carboxymethyloxy-3',4',5-trimethoxy flavone.monohydrate of formula 1 (step 5).

In step 5, the compound of formula 2 can be reacted with anhydrous alcohol instead of stirring in a medium containing water to give 7-carboxymethyloxy-3',4',5-trimethoxy flavone.solvate, which is then placed under humidified atmosphere.

(Step 1)

In step 1, 3',5,7-trihydroxy-4[1]-methoxy flavone-7-rutinoside of formula 3 is reacted with methylating reagent in a solvent in the presence of base, resulting in the conversion of hydroxyl group of carbon-3' into methoxy group, leading to the preparation of 5,7-dihydroxy-3',4'-dimethoxy flavone-7-rutinoside.

At this time, a reaction solvent has to be an aprotic solvent that cannot dissociate polar proton selected from a group consisting of dimethylformamide, dimethylsulfoxide and acetone. Base is selected from a group consisting of potassium carbonate, sodium hydroxide, potassium hydroxide and sodium carbonate. Methylating reagent can be selected from a group consisting of methyl iodide ($CH_3I$) and dimethyl sulfate ($(CH_3)_2SO_4$). Reaction temperature is 0° C.~150° C., and more preferably 0° C.~90° C.

The product obtained from the above methylating can be used as it is without further purification such as crystallization or silica gel chromatography.

According to the preparation method of the present invention, the more reactive hydroxyl group of carbon-3' than that of carbon-5 of formula 2 was converted into methoxy group. The old method for preparing the compound of formula 1 requires a special equipment to handle the pressure caused from the methylation (Yield: 76%) which is performed in closed vessel for a long time to convert both hydroxyl group into methoxy group. But, the preparation method of the present invention enables methylation under atmospheric pressure in high yield (82%).

Secondly, the crude compound obtained above is treated with acid in a solvent to give 5,7-dihydroxy-3',4'-dimethoxy flavone of formula 4.

At this time, a reaction solvent can be selected from a group consisting of dimethylformamide, tetrahydrofuran, aqueous alcoholic solution or water. Hydrochloric acid or sulfuric acid can be used for acid treatment. Reaction temperature is preferably 0° C.~100° C.

(Step 2)

In step 2, 5,7-dihydroxy-3',4'-dimethoxy flavone of formula 4 is reacted with alpha-haloacetate in which carboxyl group is protected in a solvent in the presence of base, to prepare 7-alkyloxycarbonylmethyloxy-5-hydroxy-3',4'-dimethoxy flavone of formula 5.

At this time, a reaction solvent is an aprotic solvent that cannot dissociate polar proton such as dimethylformamide, dimethylsulfoxide or acetone. Base is selected from a group consisting of inorganic base such as potassium carbonate, sodium hydroxide, potassium hydroxide and sodium carbonate; alcoholic metal salt such as sodium methoxide and sodium ethoxide; alkaline metal hydride such as sodium hydride; and alkaline earth metal hydride such as calcium hydride, and is preferred to be one of potassium carbonate, sodium hydroxide, potassium hydroxide or sodium carbonate. As alpha-haloacetate having a carboxyl group protector (R'—OCOCH$_2$X, herein R' is ethyl, methyl, t-butyl, benzyl, trichloroethyl or silyl group, and X is chlorine, bromine or iodine)', ethyl bromoacetate, methyl bromoacetate or t-butyl bromoacetate is preferably used.

(Step 3)

In step 3, the compound of formula 5 is reacted with methylating reagent to convert hydroxyl group of carbon-5 into methoxyl group to give 7-alkyloxycarbonylmethyloxy-3',4',5-trimethoxy flavone of formula 6.

This methylation is performed by the same procedure as described in step 1.

The compound obtained from the methylation can be used for the next reaction as it is without a purification process such as recrystallization or silica gel column chromatography.

(Step 4)

In step 4, the compound of formula 6 is deprotected to give 7-carboxymethyloxy-3',4',5-trimethoxy flavone of formula 2.

Deprotection procedure of reaction condition is different depending on the characteristics of R' which is a protecting group for carboxyl group of the compound of formula 6. For example, in cases that a protecting group is ethyl or methyl, the compound is treated with acid or alkali aqueous solution, and in cases that a protecting group is benzyl group, the compound is treated with hydrogen atmosphere in the presence of palladium catalyst. When the protecting group is t-butyl, benzyl or silyl group, the compound is treated with acid, and when the protecting group is trichloroethyl, the compound is treated with zinc in the presence of acid.

(Step 5)

In step 5, the compound of formula 2 is stirred in a medium containing water or left under humidity to give 7-carboxymethyloxy-3',4',5-trimethoxy flavone.monohydrate of formula 1.

Also, the compound of formula 2 is reacted with anhydrous alcohol to prepare 7-carboxymethyloxy-3',4',5-trimethoxy flavone.solvate, which is then placed under humidified atmosphere to give 7-carboxymethyloxy-3',4',5-trimethoxy flavone.monohydrate of formula 1.

Ethanol or acetone is used as a medium containing water. The crystals obtained in step 4 are stirred in aqueous medium, resulting in 7-carboxymethyloxy-3',4',5-trimethoxy flavone.monohydrate.

As anhydrous alcohol is ethanol preferred. It is also possible to leave anhydride or solvate under humidified atmosphere to give 7-carboxymethyloxy-3',4',5-trimethoxy flavone.monohydrate The preparation method for 7-carboxymethyloxy-3',4',5-trimethoxy flavone.monohydrate of the present invention reduces the long steps of total synthesis by using 3',5-7-trihydroxy-4'-methoxy flavone-7-rutinoside of formula 3, which is easily obtainable from nature, as a basic skeleton for the target compound. The preparation method according to the present invention, unlike the method described in Korea Patent No. 99-41205, methylation of the compound of formula 3 is carried out under normal pressure and without special purification procedure such as re-crystallization or chromatography. Thus, the preparation method according to the present invention does not need a special equipment to control the pressure and facilitates mass-production under mild condition, so that it is of utility value.

The present invention also provides a pharmaceutical composition containing 7-carboxymethyloxy-3',4',5-trimethoxy flavone.monohydrate represented by formula 1 as an effective ingredient. Since a pharmaceutical composition containing the compound of the present invention as an effective ingredient shows the mucus membrane protecting effect and anti-colitic effect, it can be effectively used for the protection of gastrointestinal tract including the colon and the treatment of gastrointestinal diseases as well. In particular, it can be used as protective and preventive agent for gastritis, gastric ulcer, ulcerative colitis, and Crohn's disease.

7-carboxymethyloxy-3',4',5-trimethoxy flavone.monohydrate of the present invention can be administered through various routes for effective dosage. The composition of the present invention additionally includes pharmaceutically acceptable carriers. More precisely, any pharmaceutically acceptable carrier for the informed formulation such as sterilized solution, tablet, granule, capsule, suspension, syrup, suppository and enema can be used for the composition. In general carriers can include diluents such as starch, milk, sugar, specific clay, gelatin, stearic acid, talc, vegetable oil, gum, glycols or other informed diluents. And flavoring agents, coloring additives and other components can be also included. The composition containing 7-carboxymethyloxy-3',4',5-trimethoxy flavone.monohydrate as an effective ingredient can be administrated by the formulations of oral dosage form, injection, suppository and enema, but not always limited thereto. Particularly, the composition can be prepared for oral or intravenous administration by mixing with generally used fillers, extenders, binders, wetting agents., disintegrating agents, diluents such as surfactant, or excipient. Solid formulations for oral administration are tablets, pill, dusting powders and capsules. These solid formulations are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administration are suspensions, solutions, emulsions and syrups, and the above mentioned formulations can contain various excipients such as wetting agents, sweeteners, aromatics and preservatives in addition to generally used simple diluents such as water and liquid paraffin.

Formulations for intravenous administration are sterilized aqueous solutions, water-insoluble excipients, suspensions, emulsions, suppositories or enema. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol gelatin, etc.

The effective dosage of the composition of the present invention can be determined according to weight, age, gender, health condition, diet, administration frequency, administration method, excretion and severity of a disease. In general, the effective dose of the compound is preferably 1~1000 mg/kg and is administered 1~3 times a day. The exact dosage, administration method and dosing frequency can be determined by the characteristics of a pharmaceutical form.

MODE FOR INVENTION

The molecular structure of compound of the present invention are confirmed by infrared spectroscopy, UV spectroscopy, nuclear magnetic resonance spectroscopy, mass spectrometry, thermo gravimetric analysis (TGA), and the comparison between theoretical value of elemental analysis of a compound and experimental value of it.

Practical and presently preferred embodiments of the present invention are illustrative as shown in the following Examples. However, it will be appreciated that those skilled in the art, on consideration of this disclosure, may make modifications and improvements within the spirit and scope of the present invention.

EXAMPLE 1

7-carboxymethyloxy-3',4',5-trimethoxy flavone.monohydrate (Step 1) 5,7-dihydroxy-3',4'-dimethoxy flavone 1 kg of 3',5,7-trihydroxy-4'-methoxy flavone-7-rutinoside and 454 g of potassium carbonate were dissolved in dimethylformamide at 10° C., which was heated and stirred at 90° C. for 8 hours. The reaction solution was cooled to room temperature. To the solution was added 1 kg of iodomethane, followed by stirring at room temperature for 12 hours. Upon completing the reaction, 50 L of mixed solution of ethyl acetate and dichloromethane (3:2) was added thereto. The resultant solution was stirred for 30 minutes and then filtered. 5.2 L of methanol and 5 kg of conc. hydrochloric acid were added to the filtered solid, followed by heating to reflux at 65° C. for 8 hours. The reaction mixture was cooled down to room temperature. The precipitated solid were collected by filtration and washed with a small amount of methanol to give a desired compound (yellow solid, 426 g, yield: 82%).

$^1$H NMR (DMSO-$d_6$, 400 MHz): δ3.833 (s, 3H), 3.862 (s, 3H), 6.18 (d, 1H), 6.49 (d, 1H), 6.93 (s1, H), 7.08 (d, 1H), 7.52 (d, 1H), 7.63 (dd, 1H), 10.82 (s, 1H), 12.88 (s, 1H) IR (KBr): 1636, 1590 cm$^{-1}$ (Step 2) 7-t-butyloxycarbonylmethyloxy-5-hydroxy-3',4'-dimethoxy flavone 425 g of the compound prepared in the above step 1 was dissolved in 4 L of dimethylformamide. To the solution was added 243 g of potassium carbonate and 258 g of t-butyl bromoacetate at room temperature. The resultant solution was stirred at room temperature for 5 hours. Upon completion of the reaction, water was added and extracted with ethyl acetate. The organic is layer was washed successively with water, brine and dried over anhydrous sodium sulfate. The solvent was removed by evaporation under reduced pressure. The mixed solution of ethyl acetate and hexane (volume ratio=1:3) was added to the residue, followed by stirring. Then, the product was collected by filtration to give a target compound (567 g, yield: 98%).

$^1$H NMR (DMSO-$d_6$, 400 MHz): δ1.45 (s, 9H), 3.84 (s, 3H), 3.86 (s, 3H), 4.81 (s, 2H), 6.34 (d, 1H), 6.77 (d, 1H), 7.02 (s, 1H), 7.10 (d, 1H), 7.55 (d, 1H), 7.67 (dd, 1H)

(Step 3) 7-t-butyloxycarbonylmethyloxy-3',4',5-trimethoxy flavone 330 g of the compound prepared in the above step 2 was completely dissolved in 6 L of dimethylformamide at 30° C. To the solution was added 426 g of potassium carbonate, followed by stirring for 3 hours. The reaction solution was cooled to room temperature, 330 g of iodomethane was slowly added, and stirred for 17 hours. Upon completing the reaction, water was added and extraction was performed with an excess amount of ethyl acetate. The organic layer was washed with water, brine, and dried over anhydrous sodium sulfate. The solvent was stripped off under reduced pressure. 3 L of ethyl acetate was added to the produced solid, followed by stirring at reflux for 1 hour and cooled down to room temperature. The product was collected by filtration to give a target compound (324 g, yield: 95%).

$^1$H NMR (DMSO-$d_6$, 400MHz): δ1.45 (s, 9H), 3.82 (s, 3H), 3.83 (s, 3H), 3.86 (s, 3H), 4.82 (s, 2H), 6.51 (d, 1H), 6.76 (s, 1H), 6.81 (d, 1H), 7.08 (d, 1H), 7.49 (d, 1H), 7.60 (dd, 1H)

(Step 4) 7-carboxymethyloxy-3',4',5-trimethoxy flavone 266 g of the compound prepared in the above step 3 and 172 g of p-toluene sulfonic acid were added to 1 L of the mixture of chloroform and toluene (1:1 v/v), which was heated to reflux for 3 hours and then cooled down to room temperature. The product was collected by filtration, washed with water and acetone, and dried. The dried crystals were triturated in 8 L of mixed solution of chloroform and methanol (3:1 v/v) for further stirring at room temperature for 2 hours. The washing process was repeated one more time. 220 g of target compound was obtained (yield: 95%).

$^1$H NMR (DMSO-$d_6$, 400 MHz): δ63.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H)

(Step 5) 7-carboxymethyloxy-3',4',5-trimethoxy falvone.monohydrate 220 g of the compound prepared in the above step 4-1 was added to 4 L of 95% ethanol, and stirred for 4 hours. The precipitated prduct was filtered to give a target compound (225 g, yield: 98%).

Figure 1:
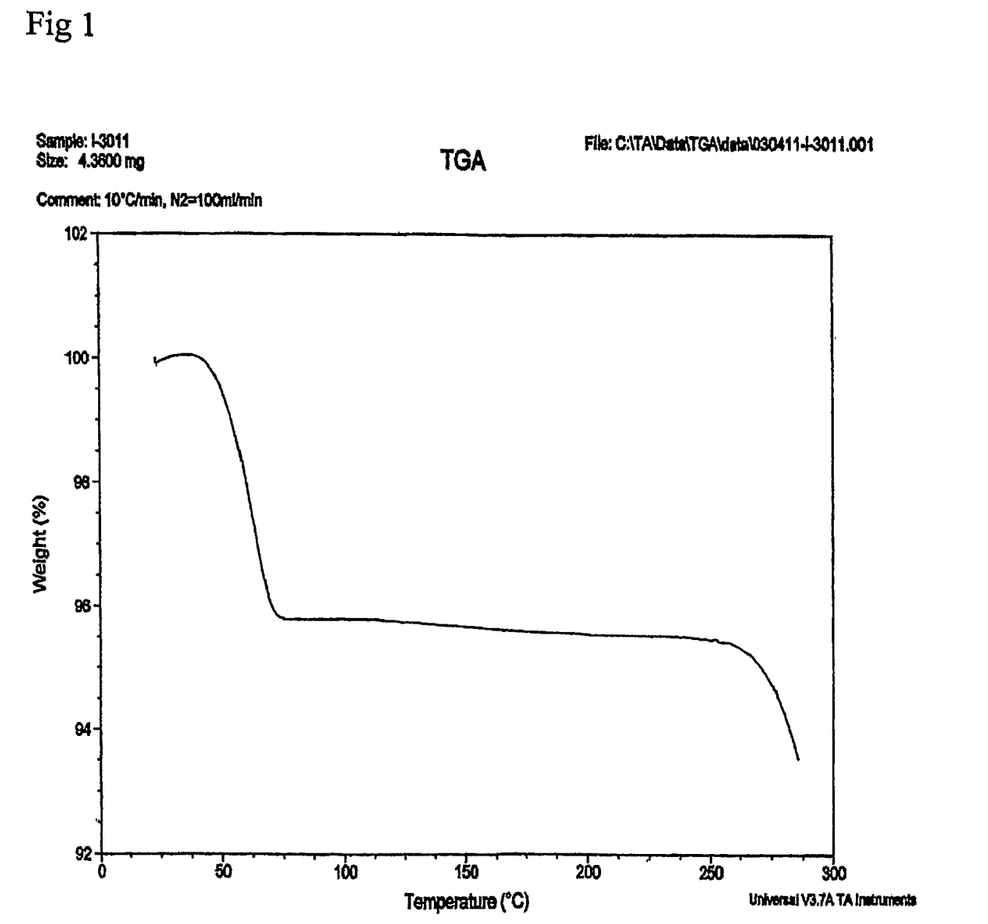
FIG. 1 is a graph showing the result of thermo gravimetric analysis of 7-carboxymethyloxy-3',4',5-trimethoxy flavone.monohydrate prepared in example 1 of the present invention.

$^1$H NMR (DMSO-$d_6$, 400 MHz): δ3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H) Elemental Analysis: Theoretical value C: 59.41%, H: 4.99%; Experimental value C: 59.46%, H: 4.85% Thermo gravimetric analysis (TGA) (see FIG. 1)

EXAMPLE 2

7-carboxymethyloxy-3',4',5-trimethoxy flavone.monohydrate (Step 1) 5,7-dihydroxy-3',4'-dimethoxy flavone A target compound was prepared by the same procedure as described in the above step 1 of example 1.

(Step 2) 7-ethyloxycarbonylmethyloxy-5-hydroxy-3',4'-dimethoxy flavone 325 g of the compound prepared in the above step 1 was dissolved in 3.3 L of dimethylformamide. To the solution were added 171 g of potassium carbonate and 137.2 ml of ethyl bromoacetate at room temperature, which was stirred for 6 hours. After completion of the reaction, the reaction mixture was added to the mixed solution of ethyl acetate and hexane (1:1 v/v). The resultant solid was collected by filtration and then put in 8.25 L of dichloromethane, and heated to reflux to for 30 minutes. The solution was cooled down to room temperature, filtered over celite pad, and concentrated under reduced pressure. The residue was triturated in a mixed solution of ethyl acetate and hexane (1:1 v/v). The product was filtered and dried to give a target compound (401 g, yield: 97%).

$^1$H NMR (DMSO-$d_6$, 400 MHz): δ1.22 (t, 3H), 3.8 4 (s, 3H), 3.87 (s, 3H), 4.18 (q, 2H), 4.93 (s, 2H), 6.39 (d, 1H), 6.83 (d, 1H), 7.04 (s, 1H), 7.12 (d, 1H), 7.57 (d, 1H), 7.69 (d, 1H)

(Step 3) 7-ethyloxycarbonylmethyloxy-3',4',5-trimethoxy flavone 210 g of the compound prepared in the above step 2 and 575 g of potassium carbonate were added to 6 L of acetone, followed by stirring at room temperature for 3 hours. To the mixture was slowly added 54.1 ml of dimethyl sulfate, and heated to reflux at 56° C. for 17 hours. Upon completing the reaction, the solution was cooled down to room temperature, to which dichloromethane was added, followed by filtering over celite pad. The filtrate was washed successively with water, brine, and dried over anhydrous sodium sulfate, and concentrated under reduced pressure. The resultant solid was put in 4 L of ethyl acetate, and stirred at ref lux for 2 hours. The solution was cooled down to room temperature, filtered and dried. 2 L of acetone was added to the produced solid, which was stirred at reflux at 56C for 2 hours. The solution was cooled down to room temperature, filtered and dried. The mentioned processes were repeated once again to give a target compound (220 g, yield: 96%).

$^1$H NMR (DMSO-$d_6$, 400 MHz): δ1.32 (t, 3H), 3.93 (s, 3H), 3.94 (s, 3H), 3.96 (s, 3H), 4.31 (q, 2H), 4.71 (s, 2H), 6.47 (d, 1H), 6.59 (d, 1H), 6.94 (d, 1H), 7.24 (s, 1H), 7.28 (d, 1H), 7.47 (dd, 1H)

(Step 4) 7-carbonylmethyloxy-3',4',5-trimethoxy flavone 165 g of the compound prepared in the above step 3 was dissolved in 800 ml of tetrahydrofuran. To the reaction solution was added 800 ml of 1 N sodium hydroxide solution, and heated to reflux for 2 hours. The reaction solution was cooled down to room temperature, and then ethyl acetate was added to the reaction solution and the organic layer was removed. The obtained water layer was washed with ethyl acetate, and acidified with 1 N hydrochloric acid aqueous solution at 0~5° C. The produced crystals were filtered and dried, followed by washing with water and acetone. The washed crystals were dried again and added to 8 L of a mixed solution of chloroform and methanol (3:1 v/v), followed by stirring at room temperature for 3 hours. The washing processes were repeated once again and dried to give a target compound (152 g, yield 99%).

$^1$H NMR (DMSO-$d_6$, 400 MHz): δ3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H)

(Step 5) (Method A) 7-carboxymethyloxy-3',4',5-trimethoxy flavone.monohydrate 2.5 L of 95% ethanol was added to 134 g of crystals obtained in the above step 4-1, and stirred for 4 hours. After filtering, the crystals were dried at 60° C. for 5 hours to give a target compound (142.6 g, yield: 99%).

Figure 2:
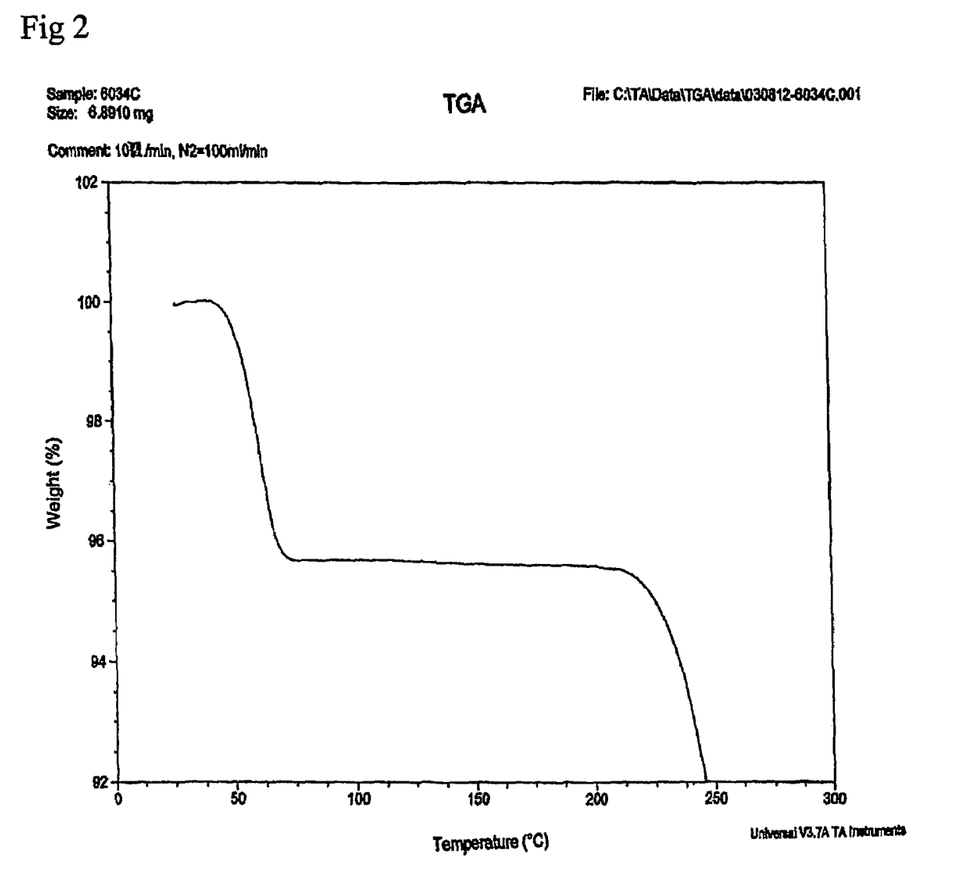
FIG. 2 is a graph showing the result of thermo gravimetric analysis of 7-carboxymethyloxy-3',4',5-trimethoxy flavone.monohydrate prepared by using aqueous ethanol solution in example 2 of the present invention.

$^1$H NMR (DMSO-$d_6$, 400 MHz): δ3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H) Elemental Analysis: Theoretical value C: 59.41%, H: 4.99%; Experimental value C: 59.17%, H: 5.10% Thermo gravimetric analysis (TGA) (see FIG. 2)

(Step 5) (Method B) 7-carbonylmethyloxy-3',4',5-trimethoxy flavone.monohydrate 400 ml of a mixed solution of acetone and water was added to 14 g of crystals obtained in the above step 4-1, and stirred for 4 hours. The solid was collected by filtration, and dried at 60° C. for 5 hours to give a target compound (14.5 g, yield: 99%).

Figure 3:
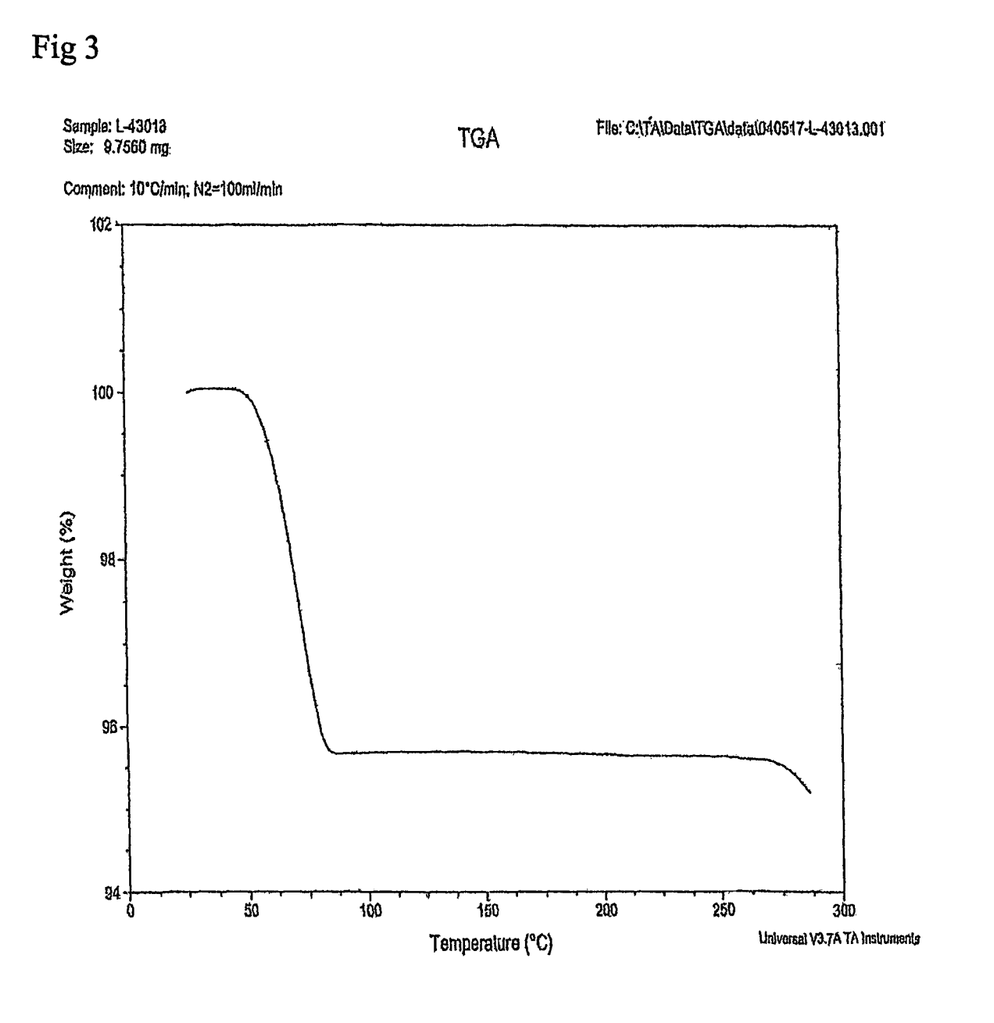
FIG. 3 is a graph showing the result of thermo gravimetric analysis of 7-carboxymethyloxy-3',4',5-trimethoxy flavone.monohydrate prepared by using aqueous acetone solution in example 2 of the present invention.

$^1$H NMR (DMSO-$d_6$, 400 MHz): δ3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H) Elemental Analysis: Theoretical value C: 59.41%, H: 4.99%; Experimental value C: 59.22%, H: 5.16% Thermo gravimetric analysis (TGA) (see FIG. 3)

EXAMPLE 3

7-carboxymethyloxy-3',4',5-trimethoxy flavone.ethanol solvate 7-carboxymethyloxy-3',4',5-trimethoxy flavone.ethanol solvate was prepared by using anhydrous ethanol, instead of 95% ethanol, and dried at 60° C. for 3 hours under reduced pressure. Other processes were the same as described in the above example 1 or example 2 (step 4-2).

Figure 4:
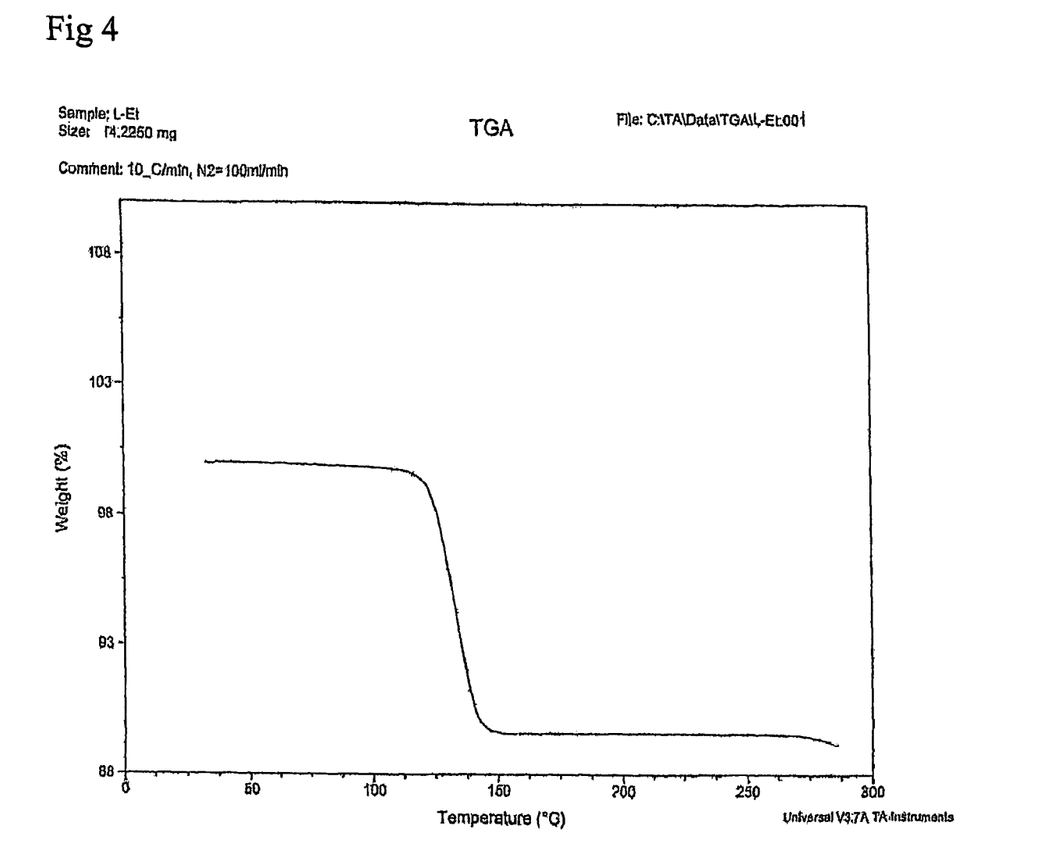
FIG. 4 is a graph showing the result of thermo gravimetric analysis of 7-carboxymethyloxy-3',4',5-trimethoxy flavone.ethanol solvate prepared in example 3 of the present invention.

$^1$H NMR (DMSO-$d_6$, 400 MHz): δ1.04 (t,3H), 3.42 (q,2H), 3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H) Elemental Analysis: Theoretical value C: 61.11%, H: 5.59%; Experimental value C: 61.25%, H: 5.32% hermo gravimetric analysis (TGA) (see FIG. 4)

COMPARATIVE EXAMPLE 7-carboxymethyloxy-3',4',5-trimethoxy flavone.anhydride 7-carboxymethyloxy-3',4',5-trimethoxy flavone.ethanol solvate prepared in the above example 3 was dried under reduced pressure at 80° C. for 5 hours to give 7-carboxymethyloxy-3',4',5-trimethoxy flavone.anhydride.

Or, 7-carboxymethyloxy-3',4',5-trimethoxy flavone.monohydrate prepared in the above example 1 or example 2 was dried under reduced pressure at 100° C. for 3 hours to give 7-carboxymethyloxy-3',4',5-trimethoxy flavone.anhydride.

Figure 5:
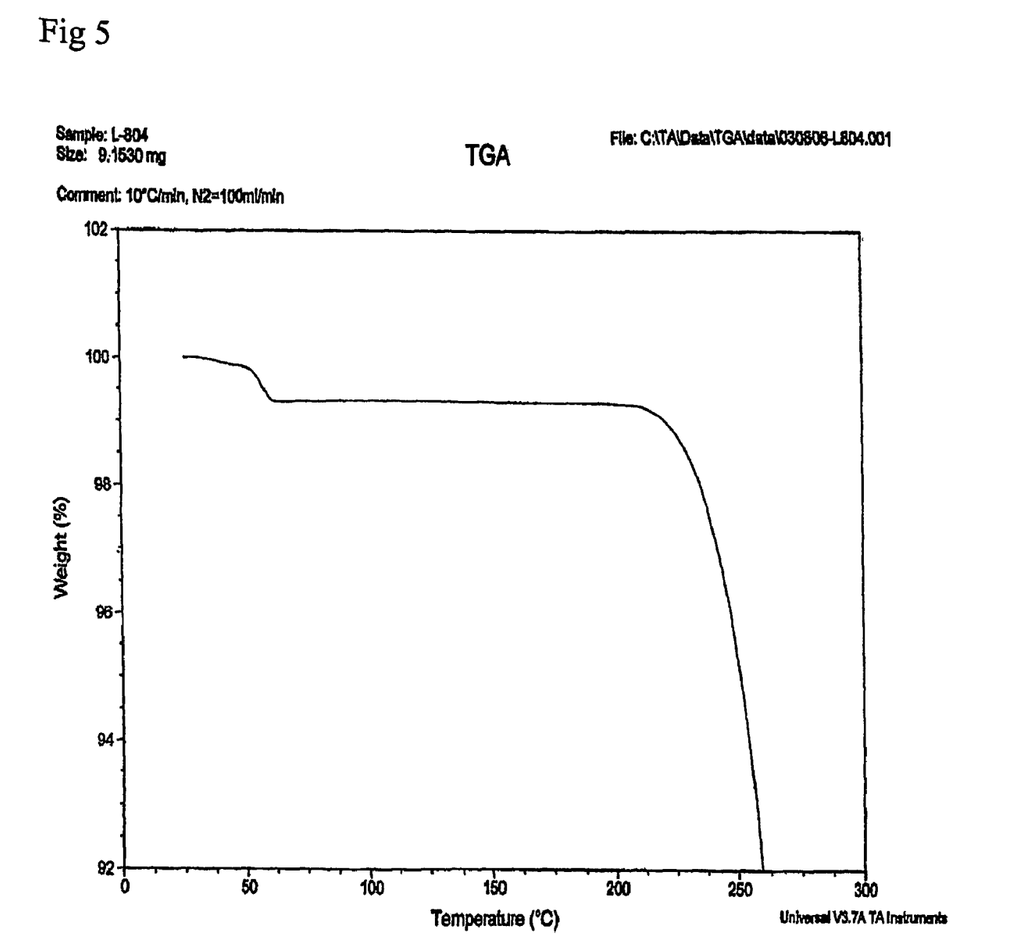
FIG. 5 is a graph showing the result of thermo gravimetric analysis of 7-carboxymethyloxy-3',4',5-trimethoxy flavone.anhydride prepared in comparative example of the present invention.

$^1$H NMR (DMSO-$d_6$, 400 MHz): δ3.82 (s, 3H), 3.83 (s, 3H), 3.86 (s, 3H), 4.85 (s, 2H), 6.52 (d, 1H), 6.77 (s, 1H), 6.85 (d, 1H), 7.08 (d, 1H), 7.50 (d, 1H), 7.65 (dd, 1H), 13.15 (br s, 1H) Elemental Analysis: Theoretical value C: 62.18%, H: 4.70%; Experimental value C: 62.15%, H: 4.73% Thermo gravimetric analysis (TGA) (see FIG. 5)

EXPERIMENTAL EXAMPLE 1

Investigation of Weight Changes of 7-carboxymethyloxy-3',4',5-trimethoxy flavone.monohydrate, ethanol solvate and anhydride 1. Hygroscopicity Test of 7-carboxymethyloxy-3',4',5-trimethoxy flavone.monohydrate and anhydride 7-carboxymethyloxy-3',4',5-trimethoxy flavone.monohydrate prepared in the above example 1 or example 2 was exactly measured by using a weighing bottle (6 cm in diameter). 1 g of the 7-carboxymethyloxy-3',4',5-trimethoxy flavone.monohydrate was prepared as a sample. The sample was kept in a vessel in which temperature was set; at 25° C.

and 75% relative humidity was maintained. Weight changes of the sample were measured after 2, 4, and 6 hours and on the first day, on the $3^{rd}$ day, and on the $6^{th}$ day. The amount of weight change was calculated as percentage to the starting weight of the sample and the results are shown in Table 1.

Weight changes of 7-carboxymethyloxy-3',4',5-trimethoxy flavone.anhydride prepared in the comparative example were also measured by the same method as mentioned above, and the results are shown in Table 1.

TABLE 1

| | Weight changes according to the time lapse (%) | | | | | |
|---|---|---|---|---|---|---|
| Sample | 0 h | 2 h | 4 h | 6 h | 1 day | 3 day | 6 day |
| Anhydride | 0 | +3.4 | +4.7 | +4.7 | +4.6 | +4.5 | +4.6 |
| Monohydrate | 0 | −0.2 | −0.3 | +0.2 | −0.3 | +0.3 | +0.3 |

*Anhydride: 7-carboxymethyloxy-3',4',5-trimethoxy flavone•anhydride
*Monohydrate: 7-carboxymethyloxy-3',4',5-trimethoxy flavone•monohydrate As shown in Table 1, 7-carboxymethyloxy-3',4',5-trimethoxy flavone.anhydride gained the weight as time passed, indicating that it absorbed moisture. After 2 hours the weight of it was 3.4% increased, and from the $4^{th}$ hour, at average 4.6% weight increase was observed. The results can be explained by the hygroscopicity of anhydrous form to monohydrate, and the extent of the weight change of 4.6% corresponds to the exact mass change from anhydrous to the monohydrate. However, 7-carboxymethyloxy-3',4',5-trimethoxy flavone.monohydrate of the present invention did not show any weight change under the same condition.

2. Test of Conversion of 7-carboxymethyloxy-3',4',5-trimethoxy flavone.ethanol solvate into monohydrate 7-carboxymethyloxy-3',4',5-trimethoxy flavone.monohydrate prepared in the above example 1 or example 2 was measured by using a weighing bottle (6 cm in diameter). 1 g of the 7-carboxymethyloxy-3',4',5-trimethoxy flavone.monohydrate was prepared as a sample. The sample was kept in a receptacle in which temperature was set at 25° C. and 75% relative humidity. On the let, $1^{st}$, $2^{nd}$, $3^{rd}$ and $6^{th}$ day, the weight of samples were measured. The extent of weight change was calculated as a percentage to the starting weight and the results are shown in Table 2

Weight changes of 7-carboxymethyloxy-3',4',5-trimethoxy flavone.ethanol solvate prepared in the above example 3 were also investigated by the same method as mentioned above, and the results are shown in Table 2.

TABLE 2

| | Weight changes according to the time lapse (%) | | | | |
|---|---|---|---|---|---|
| Sample | 0 day | 1 day | 2 day | 3 day | 6 day |
| Ethanol solvate | 0 | −4.1 | −6.5 | −6.5 | −6.5 |
| Monohydrate | 0 | −0.3 | +0.3 | +0.3 | +0.3 |

*Ethanol solvate: 7-carboxymethyloxy-3',4',5-trimethoxy flavone•ethanol solvate
*Monohydrate: 7-carboxymethyloxy-3',4',5-trimethoxy flavone•monohydrate As shown in Table 2, 7-carboxymethyloxy-3',4',5-trimethoxy flavone.ethanol solvate became lighter as time passed, indicating that it lost weight during the conversion of ethanol solvate into monohydrate. In particular, after one day of observation there was act average 4.1% weight decrease, and after two days of observation there was at average 6.5% weight decrease and constant thereafter. This weight change corresponds exactly to the weight loss from ethanolate to monohydrate. However, 7-carboxymethyloxy-3',4',5-trimethoxy flavone.monohydrate of the present invention did not show any weight change under the same conditions.

Therefore, it was confirmed that the monohydrate of the present invention has advantages in handling and storage because it does not absorb moisture in air even during long-term exposure to the humidity. So, when it is used for the formulation production of a medicine, it makes the medicine include a specific amount of an active compound consistently.

EXPERIMENTAL EXAMPLE 2

Effect on the Gastric Mucosal Damaged Model Induced by Ethanolic-HCl

In order to confirm the excellent protective effect on the gastrointestinal tract including the colon of 7-carboxymethyloxy-3',4',5-trimethoxy flavone.monohydrate of the present invention, a gastric mucosal damaged model induced by ethanol containing HCl and a inflammatory colitis model induced by trinitrobenzene sulfonic acid were used for the following experiments.

SD male rats (250-350 g) were fasted for 24 hours. The compound of the present invention was orally administered in suspension of 5% HPMC, and after 1 hour, 1.5 ml of 150 mM HCl-80% ethanol was orally administered. After 1 hour, the rats were sacrificed and the stomachs were extracted to measure ulcer index. The ulcer index was shown by the area ($mm^2$) of hemorrhage lesion (Mizui, T, et al., Jpn. J. Pharmacol. 1983, 33: 939).

Rebamipide [2-(4-chlorobenzoylamino)-3-(2-(1H)-quinolinone-4-yl)propanonic acid] (Trade Name: Mucosta) was used as a control medicine.

Results are shown in Table 3.

TABLE 3

Effects on the gastric mucosal damage induced by ethanolic-HCl in rats.

| Compound | $ED_{50}$ (mg/kg) |
|---|---|
| 7-carboxymethyloxy-3',4',5-trimethoxy flavone•monohydrate | 0.33 |
| Rebamipide | 44.2 |

As shown in Table 3, 7-carboxymethyloxy-3',4',5-trimethoxy flavone.monohydrate of the present invention has a protecting effect on the damage of gastric mucosa at least 100 times as much as Rebamipide which is known as the gastric mucous membrane protecting agent.

EXPERIMENTAL EXAMPLE 3

Experiment on the Model of Inflammatory Bowel Diseases Induced with TNBS

The modified method of Shibata et al. (Dig. Endosc. 1993, 5: 13) was used. 7 week-old male SD rats (CRJ) were fasted for a day, and the rats were put under anesthesia and canula (diameter 3 mm) was inserted into the anus to the depth of 8 cm. 25 mg/ml of TNBS (Trinitrobenzene sulfonic acid) dissolved in 50% ethanol solution was injected to each rat and the rats were positioned at feature of tail up for 1 minute.

The solution flowing out was removed and the rats were once washed with 1.5 ml of saline solution. After colitis was induced, the compound of the present invention was administered orally or rectally from the next day of inducing to the 6$^{th}$ day. For control medicine, sulfasalazine (5-amino salicylic acid) was used for oral administration and prednisolone was used for rectal administration. And for control group, 5% HPMC was administered. On the 7$^{th}$ day of experiment, each group of the rats was put under ether anesthesia for autopsy. The colon was extracted. After 1% formalin solution was injected into the cavity of the extracted colon to inflate, the both ends of it were bonded with each other, which was then fixed in 1% formalin solution for 2 hours. The all-fixed colon was cut to lengthy direction and washed to remove surrounding fat tissues and connective fissaes. Cecum was removed and the weight of the colon and the rectum was measured. The area of ulcer lesion and inflammatory region were measured to mark scores according to the criterion. Then they were fixed in 10% neutral formalin solution, and the tissue examination of lesion site was performed by a general method to mark scores according to criterion.

Clinical symptoms: Daily, clinical symptoms and survival of the animals were observed. The weight of animals was measured at the beginning day, the 3$^{rd}$ day and the 8$^{th}$ day of the experiment.

Observation with naked eye: The number and the width of the ulcer and lesion area formed in the large intestine were measured and recorded. By using modified Wallace's method (Can. J. Physiol. Pharmacol., 1988, 66: 422), lesion examined with the naked eye was scored and the average value of each group was compared. The standard of lesion scores as criterion of the damage of the colon by Wallace's method (1998) is as follows.

(0: normal, non-damaged, 1: congestion without ulcer, 2: congestion and thickening of intestinal wall without ulcer, 3: an ulcer lesion without thickening of intestinal wall, 4: more than two ulcerous/inflammatory lesion, 5: more than two ulcerous/inflammatory lesion or the length of ulcerous/inflammatory lesion is more than 1 cm, 6-10: when the length of lesion is over 2 cm, one point increases every time 1 cm of the length of ulcerous/inflammatory increases, for example: when the ulcer length is 3 cm, the point is 7)

Pathological tissue examination: The colon was trimmed at 3 cm interval from the rectum to the cecum, including the site of lesion examined with the naked eye, to make at least 4 specimens per an individual. Pathological tissue examination on the specimens was performed and the results were scored by modified method of Moyama (Ann. Clin. Lab. Sci., 1990, 20: 420). And the highest score was regarded as the score of an individual. When the lesion cannot be examined with the naked eye, the other specimen having lesion was trimmed, at 3 cm interval, from another individual.

Results are shown in Table 4 and Table 5.

TABLE 4

Effects of the compounds when orally administered on TNBS-induced colitis model

| Compound | Amount (mg/kg, p.o) | Lesion score |
| --- | --- | --- |
| 5% HPMC | | 9.0 |
| 7-carboxymethyloxy-3',4',5- | 0.3 | 7.5 |

TABLE 4-continued

Effects of the compounds when orally administered on TNBS-induced colitis model

| Compound | Amount (mg/kg, p.o) | Lesion score |
| --- | --- | --- |
| trimethoxy flavone•monohydrate | 3 | 5.9 |
| Sulfasalazine | 100 | 7.7 |

TABLE 5

Effects of the compounds when rectally administered on the TNBS-induced colitis model

| Compound | Amount (mg/kg, p.o) | Lesion score |
| --- | --- | --- |
| 5% HPMC | | 5.3 |
| 7-carboxymethyloxy-3',4',5-trimethoxy flavone•monohydrate | 0.3 | 2.0 |
| Prednisolone | 1 | 4.8 |

As shown in Table 4 and Table 5, 7-carboxymethyloxy-3',4',5-trimethoxy flavone.monohydrate of the present invention showed inhibiting effect on the TNBS-induced inflammatory colitis model by oral and rectal administration. And also, the compound of the present invention was confirmed to have better effect with a small dose than widely used conventional sulfasalazine or prednisolone.

MANUFACTURING EXAMPLE 1

Suppository 20 mg of 7-carboxymethyloxy-3',4',5-trimethoxy flavone.monohydrate was added to 1280 mg of Suppocire AP (Gatterfosse Co.) dissolved by pre-heating at 50° C., and then the solution was stirred at 50° C. for 20 minutes. The solution was cooled down to 36° C. and poured in a plastic suppository container, followed by further cooling at −5~0° C., resulting in the preparation of suppository.

MANUFACTURING EXAMPLE 2

Enema 70 mg of arginine was dissolved in 299.7 g of saline solution. To the solution was added 200 mg of 7-carboxymethyloxy-3',4',5-trimethoxy flavone.monohydrate, followed by stirring for long enough; resulting in the preparation of enema.

INDUSTRIAL APPLICABILITY

The present invention provides 7-carboxymethyloxy-3',4',5-trimethoxy flavone.monohydrate having an activity of protecting the gastrointestinal tract including the colon. With the characteristics of no hygroscopicity the compound of present invention has advantages in handling and storage under normal humidity. So for the production of a medicine, it enables us to control the consistency of the specified amount of active ingredient in each dose. The preparation method for 7-carboxymethyloxy-3',4',5-trimethoxy flavone.monohydrate of the present invention reduces the long steps of total synthesis by using 3',5,7-trihydroxy-4'-methoxyflavone-7-rutinoside, which is easily obtainable from nature, as a basic skeleton of target compound. The present invention also enables the preparation of a compound under mild conditions of atmospheric pressure for methylation, and facilitates industrial mass-production of a target compound without a special purification process such as recrystallization or column chromatography.

The invention claimed is:

1. A 7-carboxymethyloxy-3',4',5-trimethoxy flavone monohydrate represented by formula 1 having mucus protecting activity for gastrointestinal tract including colon <Formula 1>

2. A 7-carboxymethyloxy-3',4',5-trimethoxy flavone solvate represented by formula 1a

<Formula 1a>

3. The 7-carboxymethyloxy-3',4',5-trimethoxy flavone solvate as set forth in claim 2, wherein the solvent is anhydrous ethanol.

4. A preparation method of 7-carboxymethyloxy-3',4',5-trimethoxy flavone represented in scheme 3, comprising the following steps:
(1) reacting a compound of formula 3 with a methylating reagent in the presence of base to convert a hydroxyl group of carbon-3' into a methoxy group, followed by acid treatment to prepare a compound of formula 4 (Step 1);
(2) reacting the compound of formula 4 in the presence of base with alpha-haloacetate a compound of formula 5 containing a protected carboxyl group (Step 2);
(3) reacting the compound of formula 5 with a methylating agent to convert a hydroxyl group of carbon-5 into a methoxyl group, resulting in a compound of formula 6 (Step 3); and
(4) deprotecting the compound of formula 6, resulting in 7-carboxymethyloxy-3',4',5-trimethoxy flavone of formula 2 (Step 4)

<Scheme 3>

5

6

2 wherein R' is a protecting group selected from the group consisting of ethyl, methyl, t-butyl, benzyl, trichloroethyl and silyl.

5. The preparation method as set forth in claim 4, wherein a reaction solvent used in step 1 is selected from the group consisting of dimethylformamide, dimethylsulfoxide and acetone, the base of step 1 is selected from the group consisting of potassium carbonate, sodium hydroxide, potassium hydroxide and sodium carbonate, the methylating reagent of step 1 is selected from the group consisting of methyl iodide ($CH_3I$) and dimethyl sulfate (($CH_3)_2SO_4$), and the acid of step 1 is selected from the group consisting of hydrochloric acid and sulfuric acid.

6. The preparation method as set forth in claim 4, wherein a reaction temperature is 0° C.~150° C.

7. The preparation method as set forth in claim 6, wherein a reaction temperature is 0° C.~90° C.

8. The preparation method as set forth in claim 4, wherein the base used in step 2 is selected from the group consisting of inorganic bases, alcoholic metal salts, alkaline metal hydrides and alkaline earth metal hydrides.

9. A preparation method of 7-carboxymethyloxy-3',4',5-trimethoxy flavone monohydrate represented by formula 1 of claim 1, comprising:

stirring the compound of formula 2 obtained from step 4 of claim 4 in a medium containing water as shown in scheme 4

<Scheme 4>

2

10. The preparation method of 7-carboxymethyloxy-3',4',5-trimethoxy flavone monohydrate of claim 1 as set forth in claim 9, wherein the medium containing water is ethanol or acetone.

11. A preparation method of 7-carboxymethyloxy-3',4',5-trimethoxy flavone monohydrate represented by formula 1 of claim 1, comprising:

placing the compound of formula 2 obtained from the step 4 of claim 4 under humidified atmosphere as shown in scheme 5

12. A preparation method of 7-carboxymethyloxy-3',4',5-trimethoxy flavone monohydrate represented by formula 1 of claim 1, comprising:

stirring the compound of formula 2 obtained from step 4 of claim 4 in an anhydrous alcohol to give 7-carboxymethyloxy-3',4',5-trimethoxy flavone solvate represented by formula 1a; and placing the compound of formula 1a under humidified atmosphere as shown in scheme 6

13. The preparation method of 7-carboxymethyloxy-3',4',5-trimethoxy flavone monohydrate of claim 1 as set forth in claim 12, wherein the anhydrous alcohol is anhydrous ethanol.

14. A pharmaceutical composition comprising 7-carboxymethyloxy-3',4',5-trimethoxy flavone monohydrate of claim 1 as an effective ingredient.

15. A pharmaceutical composition for the protection of gastrointestinal tract including the colon and the treatment of gastrointestinal diseases comprising 7-carboxymethyloxy-3',4',5-trimethoxy flavone monohydrate of claim 1 as an effective ingredient.

16. The preparation method as set forth in claim 8, wherein the base used in step 2 is selected from the group consisting of potassium carbonate, sodium hydroxide, potassium hydroxide, sodium carbonate, sodium methoxide, sodium ethoxide, sodium hydride and calcium hydride.

17. The pharmaceutical composition of claim 15, wherein the gastrointestinal diseases are selected from the group consisting of gastritis, gastric ulcer, ulcerative colitis and Crohn's disease.

* * * * *